United States Patent [19]

Marquette et al.

[11] Patent Number: 5,077,218
[45] Date of Patent: Dec. 31, 1991

[54] EYE TRANSPORT APPARATUS

[75] Inventors: Michael M. Marquette, Portland; Michael R. Gordon, Tualatin, both of Oreg.; Emanuel Tanne, Vancouver, Wash.; Terry E. Burris, Lake Oswego; Rod Iwata, Portland, both of Oreg.

[73] Assignee: Oregon Lions Sight and Hearing Foundation Inc., Portland, Oreg.

[21] Appl. No.: 490,529

[22] Filed: May 5, 1988

[51] Int. Cl.$^5$ ............................................. A01N 1/00
[52] U.S. Cl. ......................................... 435/287; 435/1; 435/283; 435/296; 422/99; 422/104
[58] Field of Search ................... 435/1, 283, 287, 296; 623/3-6; 422/99, 102, 104; 206/438, 486, 490; 248/176

[56] References Cited

U.S. PATENT DOCUMENTS 3,676,298  7/1972  Moczar et al. ........................ 435/1
3,765,404  10/1973  Turek ..................................... 435/1
4,695,536  9/1987  Lindstrom et al. .................... 435/1

Primary Examiner—David L. Lacey
Assistant Examiner—William H. Beisner
Attorney, Agent, or Firm—Jay K. Malkin

[57] ABSTRACT

An eye transport apparatus adapted for placement within a carrying chamber is provided. The apparatus is preferably made of plastic, and includes a base having a concave upper surface sized to receive an eye globe. The center of the concave surface also includes an opening for the optic nerve. Positioned in the sides of the base are a plurality of holes and channels. The holes are designed to receive pins used to secure the optic nerve in position. The channels are designed to allow antimicrobial materials in the chamber to pass freely along the sides of the base. Finally, the apparatus includes at least one elongate stabilizing arm extending outwardly from the base. All of these features combine to provide an eye transport device which is both effective and easy to use.

21 Claims, 2 Drawing Sheets

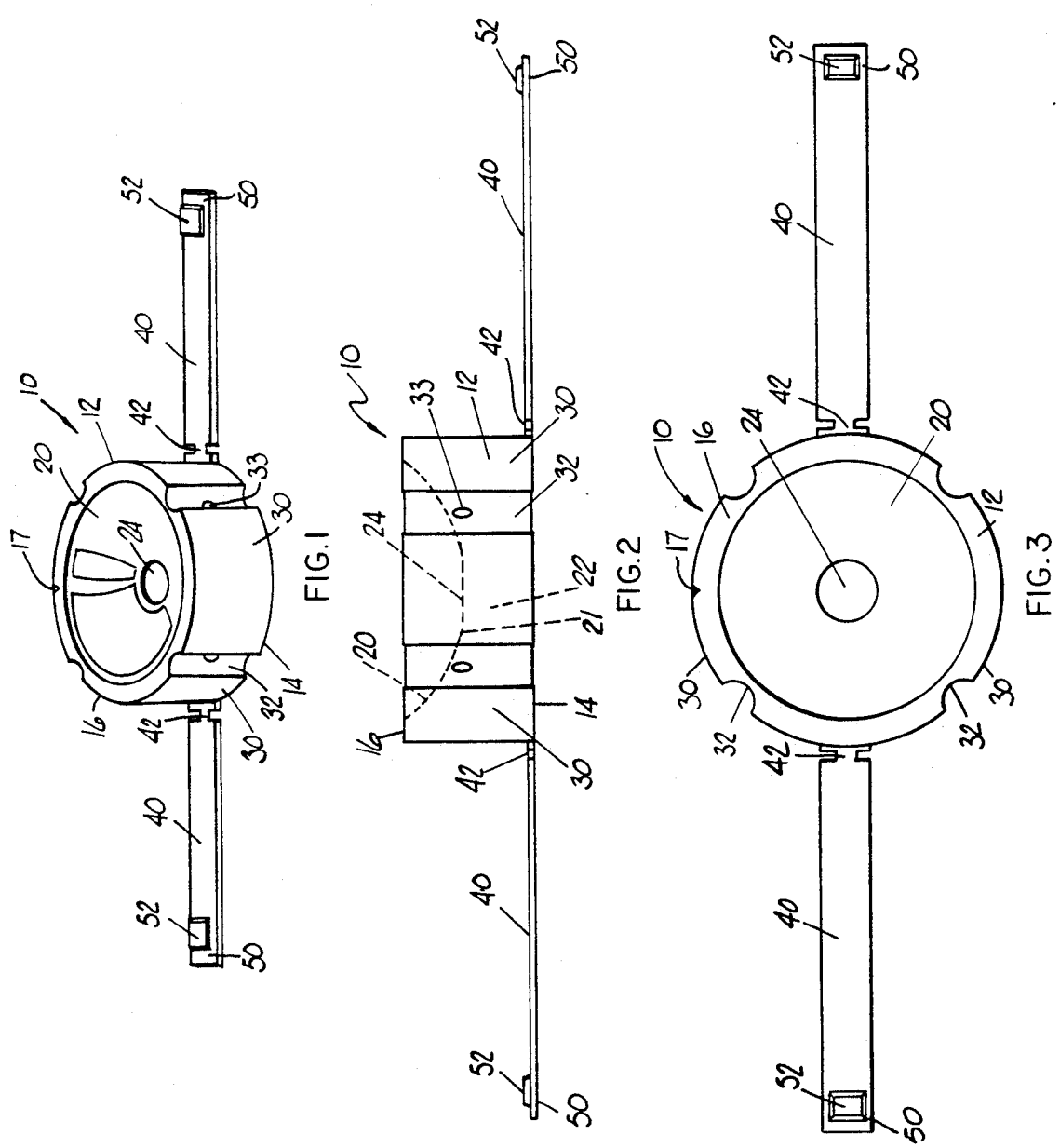

EYE TRANSPORT APPARATUS

BACKGROUND OF THE INVENTION

The present invention generally relates to eye transport devices, and more particularly to a device used by an eye bank or medical institution for transporting an eye globe in a stable and controlled manner.

Recent advances in corneal transplant technology and other eye-related surgical techniques have created a demand for devices capable of storing and/or transporting donor eye tissues. These devices, which are primarily used by eye banks and hospitals, must be capable of retaining an entire donor eye globe firmly and securely in an aseptic storage chamber so that its delicate tissues are preserved.

Within the chamber, the donor eye globe must be prevented from excess movement in order to prevent the cornea and other tissues from experiencing mechanical abrasion. Likewise, the eye globe must be stored in a manner which prevents undue physical distortion caused by inadvertent rotation of the eye globe within the chamber.

In an attempt to accomplish these goals, a device has been made consisting of a one-piece metal structure having a flat disc-like bottom to which a handle member is attached. The flat bottom includes a circular opening sized to receive the optic nerve. The eye globe rests on the flat bottom with the optic nerve extending through the opening. However, this device is often difficult to use, and does not effectively maintain the eye globe in a fixed position during transport.

Thus, a need presently exists for an eye transport apparatus which efficiently maintains a donor eye globe in position during transport without causing tissue damage. The present invention satisfies this need, and represents an advance in the art of eye transport technology, as described in greater detail below.

SUMMARY OF THE INVENTION

It is an object of the present invention to provide an eye transport apparatus which retains a donor eye globe in a fixed position during transport.

It is another object of the invention to provide an eye transport apparatus which is simple in construction and easy to use.

It is another object of the invention to provide an eye transport apparatus which facilitates stabilization of the donor eye globe during transport by selectively engaging the optic nerve, thereby preventing physical damage, abrasion and/or distortion of the globe and its delicate tissues.

It is a further object of the invention to provide an eye transport apparatus which is readily positioned within and removed from a carrying chamber having an aseptic atmosphere therein.

It is a still further object of the invention to provide an eye transport apparatus which is readily disposable, thereby eliminating procedures associated with sterilization.

It is a still further object of the invention to provide an eye transport apparatus which, when placed in a carrying chamber having antimicrobial materials therein, facilitates the maintenance of an aseptic atmosphere throughout the chamber.

It is an even further object of the invention to provide an eye transport apparatus in which the donor eye globe and corneal tissues being transported are visually unobstructed so that slit biomicroscopy photography, specular microscopy and other techniques may be used to examine the eye.

In accordance with the foregoing objects, an eye transport apparatus adapted for placement within a sealable carrying chamber is provided which enables the efficient transport of a donor eye globe. The apparatus is preferably made of a light-weight plastic, and includes a base portion having a concave upper surface sized to receive the eye globe. The center of the concave upper surface also includes an opening for receipt of the optic nerve. Positioned along the sides of the base portion are a plurality of small holes and elongate vertical channels. The holes are adapted for the insertion of pins used to secure the optic nerve in position. The channels are designed to allow antimicrobial solution vapors in the chamber to pass freely along the sides of the base portion. Finally, the apparatus includes at least one elongate, detachable arm extending outwardly from the base portion to stabilize the apparatus and eye globe within the chamber. The arm also facilitates insertion and removal of the apparatus from the chamber. All of these features combine to provide an eye transport device which is effective, easy to use, and inexpensive.

These and other objects, features, and advantages of the invention will become apparent from the following drawings and detailed description of a preferred embodiment.

BRIEF DESCRIPTION OF THE DRAWINGS

FIG. 1 is a perspective view of an eye transport apparatus in accordance with the present invention prior to insertion thereof in a carrying chamber;

FIG. 2 is a side view of the invention;

FIG. 3 is a top view of the invention; and .

DETAILED DESCRIPTION OF A PREFERRED EMBODIMENT

Figure 4:
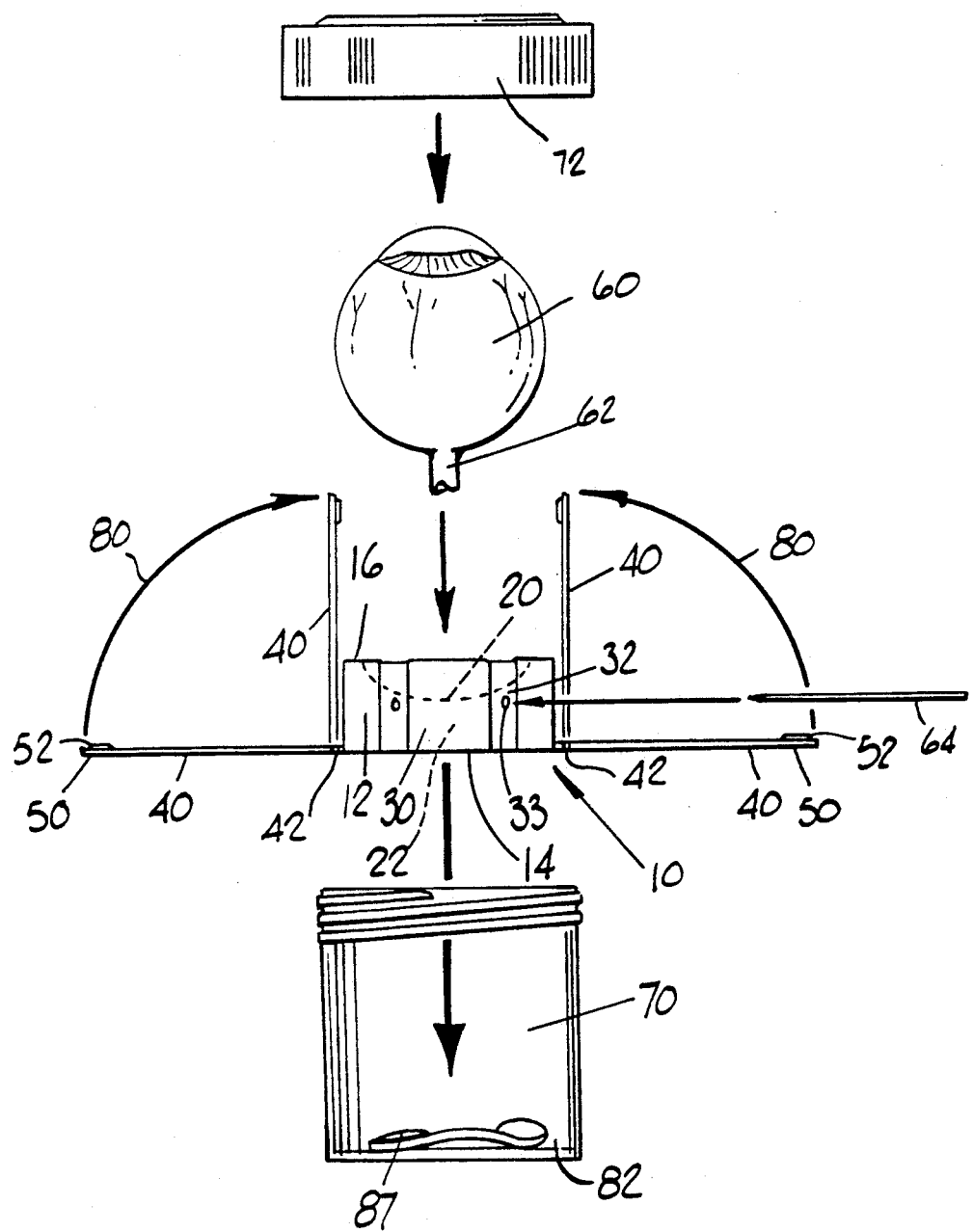
FIG. 4 is a side view of the invention showing its relationship to a donor eye globe, carrying chamber, and optic nerve retaining pin.

The present invention involves an improved eye transport apparatus designed for use by eye banks and medical institutions. It is adapted for placement in a sealable carrying chamber having antimicrobial materials therein, as described in detail below.

With reference to FIG. 1, the eye transport apparatus 10 of the present invention is illustrated. The entire apparatus 10 is preferably constructed of a thin, disposable, and chemically-inert plastic. An exemplary plastic for this purpose would include polypropylene. It is desirable that the apparatus 10 be constructed of disposable plastic in order to eliminate the sterilization problems associated with reusable metal devices. Also, the apparatus 10 is preferably of single-piece construction in order to facilitate mass production of the device by conventional molding or stamping techniques.

As shown in FIGS. 1-3, the apparatus 10 includes a base 12 which is preferably cylindrical in shape and of hollow construction. The base 12 includes a flat open bottom 14 and a top portion 16. The flat bottom 14 is designed to ensure that the apparatus 10 remains stable in its carrying chamber and does not tip. The top portion 16 may include at least one optional marking or indentation 17 designed to facilitate orientation of the eye globe relative to the base.

The top portion 16 further includes a concave upper surface 20 contoured to receive the donor eye globe. The shape of the concave surface 20 is designed to prevent undue distortion of the globe during transport. It also assists in retaining the globe in position in order to eliminate abrasion through inadvertent globe dislocation.

As previously described, the apparatus 10 is preferably of one-piece construction. In accordance with this design, the lower face 21 of the concave surface 20 is sufficiently spaced from the flat bottom 14 to form an open zone 22 therebetween FIG. 2). The purpose of zone 22 will be described hereinbelow.

It is anticipated that the base 12 may be of any suitable size, depending on the size of its associated storage chamber. However, tests have shown that a cylindrical base 12 with a diameter of about 32 mm and height of about 12 mm will work adequately with most storage chambers available today. Immediately prior to corneal excision, the base 12 and eye globe are immersed within an antimicrobial solution. For practical reasons, it is desired that the amount of solution for this purpose be minimized. To accomplish this, the height of the base 12 should be as low as possible.

Positioned in the center of the concave upper surface 20 is maintaining means in the form of an opening 24 sized for insertion of the eye globe optic nerve (FIGS. 1 and 3). The opening 24 is most often between 6.5 and 8.0 mm in diameter, with about 7.0 mm being preferred. Placement of the optic nerve within the opening 24 assists in maintaining the optic nerve and eye globe in a fixed position relative to the base 12 during transport. This again reduces the risk of mechanical abrasion to the cornea.

With reference to FIGS. 2 and 3, the sides 30 of the base 12 further include at least one and preferably four vertical channels 32 extending continuously from the flat bottom 14 to the top portion 16 of the base 12. As further described below, the apparatus 10 is designed to be placed in a sealable carrying chamber having antimicrobial materials therein. This prevents bacterial degradation of the eye globe and keeps it moist. Each channel 32 should be sufficiently large to allow the passage of antimicrobial vapors or solution freely in the chamber from the flat bottom 14 of the base 12 to the top portion 16 and vice versa. An exemplary channel for this purpose would be approximately 12 mm long, 4 mm wide, and 1.5 mm deep.

Also included in the sides 30 of the apparatus 10, and preferably within the channels 32 are pin holes 33. As illustrated in FIG. 2, the pin holes 33 are positioned directly beneath the lower face 21 of the concave surface 20, and provide access to the open zone 22 in the base 12. The pin holes 33 (which are preferably about 1 mm in diameter) are sized for the insertion of metal pins designed to engage the optic nerve which extends through opening 24 in the base 12. This further stabilizes the donor eye globe during transport.

As shown in FIGS. 1-3, the base 12 further includes at least one and preferably two stabilizing arms 40 which are attached to the base 12 adjacent the flat bottom 14. Each arm 40 is secured to the base 12 using a narrow frangible joint 42 which enables each arm 40 to be readily detached from the base 12, if desired. Detachment is frequently desired in order to facilitate access to the eye globe for corneal/scleral excision.

The length of each arm 40 is determined by the overall height of the carrying chamber with which the apparatus 10 is used. However, each arm 40 should preferably extend to within about 1 mm of the inside surface of the chamber lid. The arms 40 are designed to engage the donor eye globe and interior walls of the chamber in order to keep the eye globe and apparatus 10 from shifting inside the chamber if the chamber is turned on its side or rotated. Furthermore, the extraocular muscles of the eye globe may be pinned to the arms 40 for additional stabilization if desired. The arms 40 also facilitate removal and insertion of the apparatus 10 from the chamber.

The outer end 50 of each arm 40 further includes at least one protrusion 52 (FIGS. 1 and 2) which may be rectangular in design. Each protrusion 52 is used as a grasping surface for forceps or the like in order to facilitate removal of the apparatus 10 from its associated chamber. An exemplary rectangular protrusion 52 suitable for this purpose would be about 3 mm wide and about 3 mm long.

FIG. 4 shows the apparatus 10 in relation to a donor eye globe 60 having an optic nerve stump 62. Also shown is an optic nerve retaining pin 64 to be inserted within each pin hole 33 in the sides 30 of the base 12.

As discussed herein, the apparatus 10 is designed for placement within a carrying chamber 70 having a lid 72. Immediately prior to placement of the apparatus 10 in the carrying chamber 70, the arms 40 fold upward as illustrated by arrows 80 in FIG. 4. The entire apparatus 10 rests on the bottom 82 of the chamber 70, with an antimicrobial solution-soaked pad 87 being positioned directly beneath the base portion 12 partially or entirely within open zone 22.

In use, the eye transport apparatus of the present invention is capable of efficiently transporting a donor eye globe in a highly stable manner. Its design facilitates examination of the eye globe prior to surgery, in that there are no components which visually obstruct the globe/cornea. In this regard, the invention is designed to eliminate the need for elevating the eye globe in the chamber for examination, thereby reducing the potential for contamination or accidental dropping of the globe.

Finally, since the invention is preferably manufactured from disposable plastic, sterilization procedures normally associated with metal transport devices are eliminated, thereby reducing costs and minimizing the chances of disease transmission to eye bank/medical personnel.

Having described a preferred embodiment of the present invention, it is anticipated that suitable modifications may be made thereto within the scope of the invention. Accordingly, the invention shall only be construed in accordance with the following claims.

What is claimed is:

1. An eye globe transport apparatus comprising:
   a base having a flat bottom portion, a top portion, and side portions therebetween, said top portion comprising a concave surface constructed so as to receive an eye globe; and
   maintaining means within said base for enabling an optic nerve of the eye globe to be maintained in a fixed position relative to said base, said maintaining means comprising an opening in said concave surface of said top portion of said base constructed so as to receive the optic nerve, the receipt of the optic nerve in said opening limiting the movement of the eye globe within said concave surface of said top portion of said base.

2. An eye globe transport apparatus comprising:
a base having a flat bottom portion, a top portion, and side portions therebetween, said top portion comprising a concave surface constructed so as to receive an eye globe;
maintaining means within said base for enabling an optic nerve of the eye globe to be maintained in a fixed position relative to said base, said maintaining means comprising an opening in said concave surface of said top portion of said base constructed so as to receive the optic nerve, the receipt of the optic nerve in said opening limiting the movement of the eye globe within said concave surface of said top portion of said base; and
means within said base for preventing the removal of the optic nerve from said opening in said concave surface of said top portion of said base after the optic nerve is inserted in said opening.

3. The eye globe transport apparatus of claim 2 further comprising at least one vertical channel in said base extending from said bottom portion to said top portion thereof along said side portions.

4. The eye globe transport apparatus of claim 2 wherein said concave surface of said top portion of said base is sufficiently spaced from said flat bottom portion of said base to form an open zone therebetween.

5. The eye globe transport apparatus of claim 2 wherein said means for preventing the removal of the optic nerve from said opening comprises at least one aperture through said side portions of said base and at least one pin, said aperture being positioned beneath said concave surface of said top portion of said base and constructed so as to receive said pin therethrough, said pin engaging the optic nerve after passage of the optic nerve through said opening in said concave surface of said top portion of said base.

6. The eye globe transport apparatus of claim 2 further comprising stabilization means for maintaining said apparatus and the eye globe in a fixed position when transported in a carrying chamber having a top portion, bottom portion, and side walls.

7. The eye globe transport apparatus of claim 2 wherein said apparatus is of single-piece construction.

8. The eye globe transport apparatus of claim 2 wherein said apparatus comprises plastic.

9. The eye globe transport apparatus of claim 8 wherein said plastic comprises polypropylene.

10. An eye globe transport apparatus comprising:
a base having a flat bottom portion, a top portion, and side portions therebetween, said top portion comprising a concave surface constructed so as to receive an eye globe;
stabilization means for maintaining said apparatus and the eye globe in a fixed position when transported within a carrying chamber; and
maintaining means within said base for enabling an optic nerve of the eye globe to be maintained in a fixed position relative to said base.

11. The eye globe transport apparatus of claim 10 wherein said maintaining means for enabling the optic nerve of the eye globe to be maintained in a fixed position comprises an opening in said concave surface of said top portion of said base constructed so as to receive the optic nerve, the receipt of the optic nerve in said opening limiting the movement of the eye globe within said concave surface of said top portion of said base.

12. The eye globe transport apparatus of claim 11 wherein said concave surface of said top portion of said base is sufficiently spaced from said flat bottom portion of said base to form an open zone therebetween.

13. The eye globe transport apparatus of claim 12 further comprising means within said base for preventing the removal of the optic nerve from said opening in said concave surface of said top portion of said base after the optic nerve is inserted in said opening, said means for preventing comprising at least one aperture through said side portions of said base and at least one pin, said aperture being positioned beneath said concave surface of said top portion of said base and constructed so as to receive said pin therethrough, said pin extending into said open zone for engagement with the optic nerve after passage of the optic nerve through said opening of said concave surface of said top portion of said base.

14. An eye globe transport apparatus comprising:
a base having a flat bottom portion, a top portion and side portions therebetween, said top portion comprising a concave surface constructed so as to receive an eye globe and an opening in said concave surface constructed so as to receive an optic nerve of the eye globe, said top portion of said base being sufficiently spaced from said flat bottom portion to form an open zone therebetween, said base being constructed so as to be received within a carrying chamber having a top portion, bottom portion and side walls;
at least one vertical channel in said base extending from said bottom portion to said top portion thereof along said side portions;
at least one aperture through said side portions of said base and at least one pin, said aperture being positioned beneath said concave surface of said top portion of said base and constructed so as to receive said pin therethrough, said pin extending into said open zone for engagement with the optic nerve after passage of the optic nerve through said opening in said concave surface of said top portion of said base; and
at least one arm member pivotally attached to and extending outwardly from said base, said arm member being constructed so as to engage said side walls of the carrying chamber in order to prevent said apparatus from moving therein, said arm member comprising a frangible attachment joint used to attach said arm member to said base in a manner wherein said arm member may be readily detached from said base, said arm member further comprising at least one outwardly extending protrusion constructed so as to facilitate grasping of said apparatus to enable removal of said apparatus from the carrying chamber.

15. The eye globe transport apparatus of claim 14 wherein said apparatus is of single-piece construction.

16. The eye globe transport apparatus of claim 14 wherein said apparatus comprises plastic.

17. The eye globe transport apparatus of claim 16 wherein said plastic comprises polypropylene.

18. The eye globe transport apparatus comprising:
a base having a flat bottom portion, a top portion, and side portions therebetween, said top portion comprising a concave surface constructed so as to receive an eye globe;
stabilization means for maintaining said apparatus and the eye globe in a fixed position when transported within a carrying chamber having walls, said stabilization means comprising at least one arm member attached to and extending outwardly from said base, said arm member being constructed so as to engage the side walls of the carrying chamber in order to prevent said apparatus from moving therein; and maintaining means within said base for enabling an optic nerve of the eye globe to be maintained in a fixed position relative to said base.

19. The eye globe transport apparatus of claim 18 wherein said arm member is pivotally attached to said base, thereby allowing movement of said arm member relative to said base.

20. The eye globe transport apparatus of claim 18 wherein said arm member further comprises a frangible attachment joint used to attach said arm member to said base in a manner wherein said arm member may be readily detached from said base.

21. The eye globe transport apparatus of claim 18 wherein said arm member further comprises at least one outwardly extending protrusion constructed so as to facilitate grasping of said apparatus to enable removal of said apparatus from the carrying chamber.

* * * * *

UNITED STATES PATENT AND TRADEMARK OFFICE
CERTIFICATE OF CORRECTION

PATENT NO. : 5,077,218
DATED : 12/31/91
INVENTOR(S) : Michael M. Marquette et al.

It is certified that error appears in the above-identified patent and that said Letters Patent is hereby corrected as shown below:

In column 6, on line 60 (claim 18), please delete "The" and insert therefor --An--.

In column 6, on line 67, before "walls" please insert --side--.

Signed and Sealed this

Thirteenth Day of April, 1993

Attest:

STEPHEN G. KUNIN

Attesting Officer    Acting Commissioner of Patents and Trademarks